United States Patent
Harant et al.

(10) Patent No.: US 10,267,776 B2
(45) Date of Patent: Apr. 23, 2019

(54) METHOD FOR ESTIMATING A RETENTION TIME IN A CHROMATOGRAPHY COLUMN

(71) Applicant: Commissariat A L'Energie Atomique et aux Energies Alternatives, Paris (FR)

(72) Inventors: Olivier Harant, Saint-Egreve (FR); Francois Bertholon, La Tronche (FR); Pierre Grangeat, Saint-Ismier (FR)

(73) Assignee: Commissariat A L'Energie Atomique et aux Energies Alternatives, Paris (FR)

( * ) Notice: Subject to any disclaimer, the term of this patent is extended or adjusted under 35 U.S.C. 154(b) by 212 days.

(21) Appl. No.: 15/241,173

(22) Filed: Aug. 19, 2016

(65) Prior Publication Data

US 2017/0052158 A1    Feb. 23, 2017

(30) Foreign Application Priority Data

Aug. 20, 2015  (FR) ..................... 15 57848

(51) Int. Cl.
  *G01N 30/60*  (2006.01)
  *G01N 30/86*  (2006.01)
(52) U.S. Cl.
  CPC ..... *G01N 30/8693* (2013.01); *G01N 30/6073* (2013.01)
(58) Field of Classification Search
  None
  See application file for complete search history.

(56) References Cited

PUBLICATIONS

French Preliminary Search Report dated Jun. 30, 2016 in French Application 15 57848, filed on Aug. 20, 2015 ( with English translation of Categories of Cited Documents and Written Opinion).
M. Wernekenschnieder et al. "Monte-Carlo Simulation of Gas Chromatographic Separation for the Prediction of Retention Times and Peak Half Widths", Chromatographia, vol. 28, No. 5-6, 1989, 8 pages.
J.B. Phillips et al. "Probabilistic Approach to Digital Simulation of Chromatographic Processes", Separation Science and Technology, vol. 16, 1981, 24 pages.
Francesco Dondi et al. "Monte Carlo Model of Nonlinear Chromatography", Analytical Chemistry, vol. 72, No. 18, 2000, 10 pages.
Attila Felinger "Molecular dynamic theories in chromatography", Journal of Chromatography A, vol. 1184, 2008, 22 pages.

*Primary Examiner* — Roy Y Yi
*Assistant Examiner* — Geoffrey T Evans
(74) *Attorney, Agent, or Firm* — Oblon, McClelland, Maier & Neustadt, LLP (57) ABSTRACT

The invention is a method for estimating a retention time of a particle in a chromatography column, and more particularly in a chromatography column one parameter of which, such as temperature, is modulated. The retention time is estimated on a probabilistic basis by sequentially modelling the transit of the particle in the column. When this stochastic approach is adopted for a set of particles of a given type, it allows a statistical distribution of the retention time in the column to be determined.

9 Claims, 5 Drawing Sheets

METHOD FOR ESTIMATING A RETENTION TIME IN A CHROMATOGRAPHY COLUMN

TECHNICAL FIELD

The technical field of this patent application is the analysis of chemical or biological species by chromatography, and more particularly modelling of a chromatography signal.

PRIOR ART

Chromatography is a very commonly used technique for analyzing chemical species in gaseous or liquid media. This analysis technique is based on chromatography columns, the operating principle of which is well known: a particle carried by a fluid, called the carrier fluid, also designated by the expression mobile phase, transits a channel between an entrance and an exit. The wall of the channel includes a coating, called the stationary phase, with which the particle has an affinity such that the particle is capable of being momentarily adsorbed then desorbed. Depending on the affinity with the stationary phase, the transit of the particle through the channel may take more or less time. A chromatography column also includes a detector, placed at the exit of the channel, for detecting the presence of the particle when the latter exits the channel.

Generally, the signal detected by the detector takes the form of a histogram representing the number of detections as a function of time, this histogram being designated by the term chromatogram.

When various particles of various species are injected at the same time into a column, the transit time of each particle depends on its affinity with the stationary phase and hence on the chemical nature of the particle. Thus, the chromatogram contains various peaks, each peak representing the distribution of the particle transit times of a given species in the column.

The chromatogram may be modelled as a function of each particle species, as has been widely described in the literature. This modelling corresponds to the definition of what is referred to as a direct model, allowing a chromatogram to be estimated if the nature of the introduced particles is known. This is for example described in patent application WO201026228, the latter describing modelling a chromatogram with a spatial-temporal model.

The transit of the particle through the column depends on operating parameters of the column, these parameters having an influence on the adsorption or desorption of the particle. It may be a question of the temperature of the column or the composition of the mobile or stationary phase. In order to obtain a better separation between particles of different chemical species, these operating parameters may be modulated. For example, the temperature or the composition of the mobile phase may vary temporally between the entrance and exit of the particle. It may also be the stationary phase that is modulated, its composition varying spatially so that during the transit of the particle the adsorption and/or desorption properties vary temporally. As a result of this modulation, whether it be temporal or spatial, the adsorption and desorption properties of the stationary phase with respect to each type of particle are modified.

However, prior-art chromatogram models are based on average particle behaviors described by deterministic models. These approaches are not suitable for a situation in which an operating parameter of the column varies during the transit of the particle through the column.

The inventors have determined a modelling method allowing a direct model to be determined that is applicable to chromatography columns one, or even more than one, of the operating parameters of which varies during the transit of a particle through the column.

SUMMARY OF THE INVENTION

One subject of the invention is a method for estimating a retention time of a particle in a chromatography column, as claimed in one of the appended claims.

The invention is based on a description of the individual behavior of a molecule during its passage through the column, according to what is called a sampling technique. This microscopic approach makes it possible to take into account a variation in a parameter governing the operation of the column during the transit of a molecule. By describing the behavior of a set of molecules of a given species, including a number of molecules considered to be sufficiently representative, the invention allows a distribution of the retention time corresponding to said species to be established, on the basis of which it is possible to determine statistical indicators—in particular the average, variance or other times.

The invention will be better understood on reading the following description of exemplary embodiments, which are based on the following figures.

DESCRIPTION OF PARTICULAR EMBODIMENTS

Figure 1:
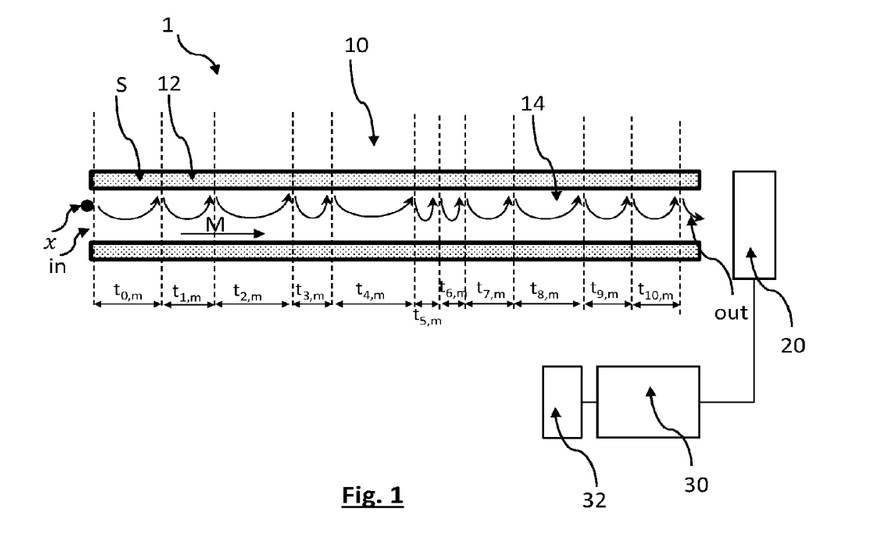
FIG. 1 shows a chromatography column.

FIG. 1 shows a chromatography column 1 including a channel 10 and a detector 20. The wall of the channel 10 includes a coating 12 called the stationary phase S. The channel also includes a central portion 14 through which a carrier fluid is able to flow between an entrance in and an exit out. Such a carrier fluid is generally designated by the expression mobile phase M.

The carrier fluid may be a gas or a liquid the affinity of which with the stationary phase S is negligible so that the carrier fluid does not interact with the stationary phase during its transit through the column. Its transit time through the column, i.e. between the entrance and the exit of the column, is designated by the term dead time, and denoted $t_0$. This dead time $t_0$ corresponds to the transit time of a particle that does not interact with the stationary phase.

The function of the carrier fluid is to transport a particle x between the entrance and the exit of the channel. During its transit through the column, the particle x interacts with the stationary phase S, thereby causing a plurality of adsorptions/desorptions. Between each adsorption, the particle is carried by the mobile phase M, and moves at the same speed as the latter. In FIG. 1, the path of the particle x, through the column 1, is represented by a succession of arrows, each arrow showing the transit of the particle x between two successive adsorptions. The times passed between each adsorption are also shown. They are designated by $t_{0,m}$ (between the entrance and the first adsorption), $t_{1,m}$ (between the first and second adsorption), $t_{2,m}$, $t_{3,m}$, $t_{4,m}$, $t_{5,m}$, $t_{6,m}$, $t_{7,m}$, $t_{8,m}$, $t_{9,m}$, and $t_{10,m}$. Generally, the time $t_{i,m}$ designates the time passed in the mobile phase by a particle x following an $i^{th}$ adsorption, i being a positive integer comprised between 0 and $N_i$, $N_i$ representing a number of adsorptions undergone by the particle x in the column.

A detector 20 is placed at the exit of the channel, said detector being able to emit a signal representative of the number of particles exiting from the column as a function of time. This signal corresponds to the chromatogram mentioned in the description of the prior art.

The detector 20 is able to be connected to a processor 30; the latter is connected to a memory 32 containing instructions, the latter being able to be executed by the processor 30 in order to allow the method shown in FIG. 2, 3A or 3B and described below to be implemented. These instructions may be saved on a processor-readable storage medium such as a hard disk, CD-ROM or another type of memory.

The inventors chose to model the chromatogram, i.e. to determine a direct model of the column, using an original approach based on a stochastic model, by simulating, sequentially and randomly, the individual transit of a particle using probability laws describing the behavior of the particle in the column. The simulation of many particles x of a given species X then allows a statistical distribution relating to their transit time in the column, which time is also called the retention time $t_R$, to be obtained. Such a distribution constitutes the direct model of the column with respect to said particle species.

By "the particle", what is meant is a chemical or biological entity able to be detected by the detector. It is for example a question of a molecule, a protein, a peptide, a molecular aggregate, a molecular complex, a nanoparticle.

By "particle of a given species", what is meant is a particle of given chemical nature or a particle constituted by the same chemical elements. In the rest of the description, the index X designates a particle species, whereas the index x designates an individual particle.

The modelling is based on the use of:
a probability law of the time passed by the particle in the mobile phase before or after each adsorption in the stationary phase, this probability law being designated below by the expression first probability law.
a probability law of the time passed by the particle in the stationary phase, during each adsorption, this probability law being designated below by the expression second probability law.

The first and second probability laws also depend on the species X of each particle and on parameters P governing the operation of the chromatography column.

Generally, to determine the times passed:
between each adsorption, in the mobile phase,
during each adsorption, in the stationary phase, the transit of a particle through the column is described by successive random samples according to the first and second probability laws, respectively.

As mentioned above with respect to the prior art, the operation of the column 1 is governed by operating parameters P, called parameters, the latter having an influence on the adsorption and the desorption of the particle. Such operating parameters are for example:
the temperature T of the column;
the composition of the mobile phase, in particular in the case where it is a liquid;
the composition of the stationary phase.

These parameters may vary as the particle passes through the column. The temperature and/or the composition of the mobile phase may be modulated temporally, whereas the composition of the stationary phase may be modulated spatially, between the entrance in and the exit out of the column.

In the embodiments described below, the first and second probability laws follow exponential distributions, respectively parameterized by an adsorption rate $k_{a,X,P}$ and a desorption rate $k_{d,X,P}$. The adsorption rate $k_{a,X,P}$ corresponds to the probability per unit time that a particle x of the species X present in the mobile phase is adsorbed in the stationary phase given the operating parameters P. Its inverse $$\frac{1}{k_{a,X,P}}$$

corresponds to an average time passed by the particle in the mobile phase, between two successive adsorptions. The desorption rate $k_{d,X,P}$ corresponds to the probability per unit time that a particle x of the species X present in the stationary phase will be desorbed given the operating parameters P. Its inverse $$\frac{1}{k_{d,X,P}}$$

corresponds to an average time passed by the particle in the stationary phase, following an adsorption. The adsorption and desorption rates are known and may be stored in the memory 32.

Thus, the first and second probability laws may respectively be written:

$$f_m(t,k_{a,X,P})=k_{a,X,P}\times e^{-t\times k_{a,X,P}} \qquad (1)$$

$$f_m(t,k_{d,X,P})=k_{d,X,P}\times e^{-t\times k_{d,X,P}} \qquad (2)$$

It will be understood that the index P designates either one, or more than one operating parameter.

Figure 2:
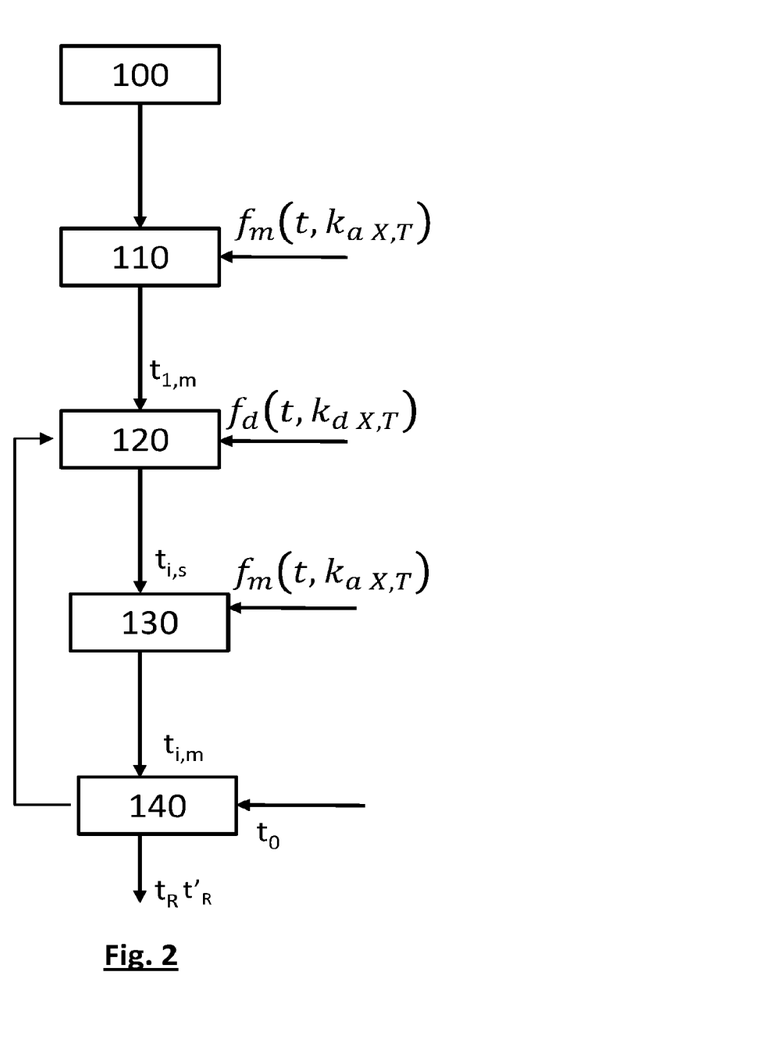
FIG. 2 shows the steps of a method according to a first embodiment of the invention.
Figure 3A:
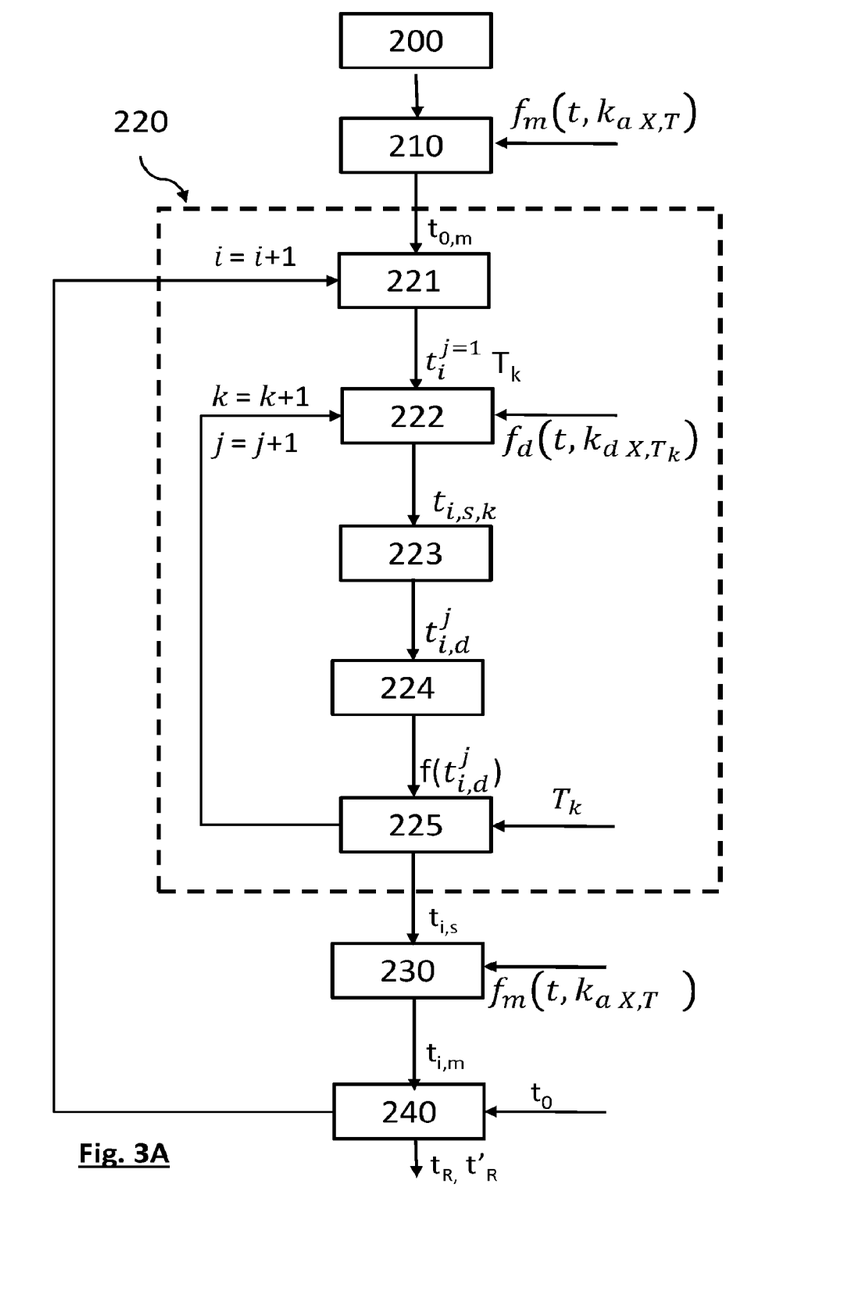
FIGS. 3A and 3B show the steps of a method according to a second and third embodiment of the invention, respectively.
Figure 3B:
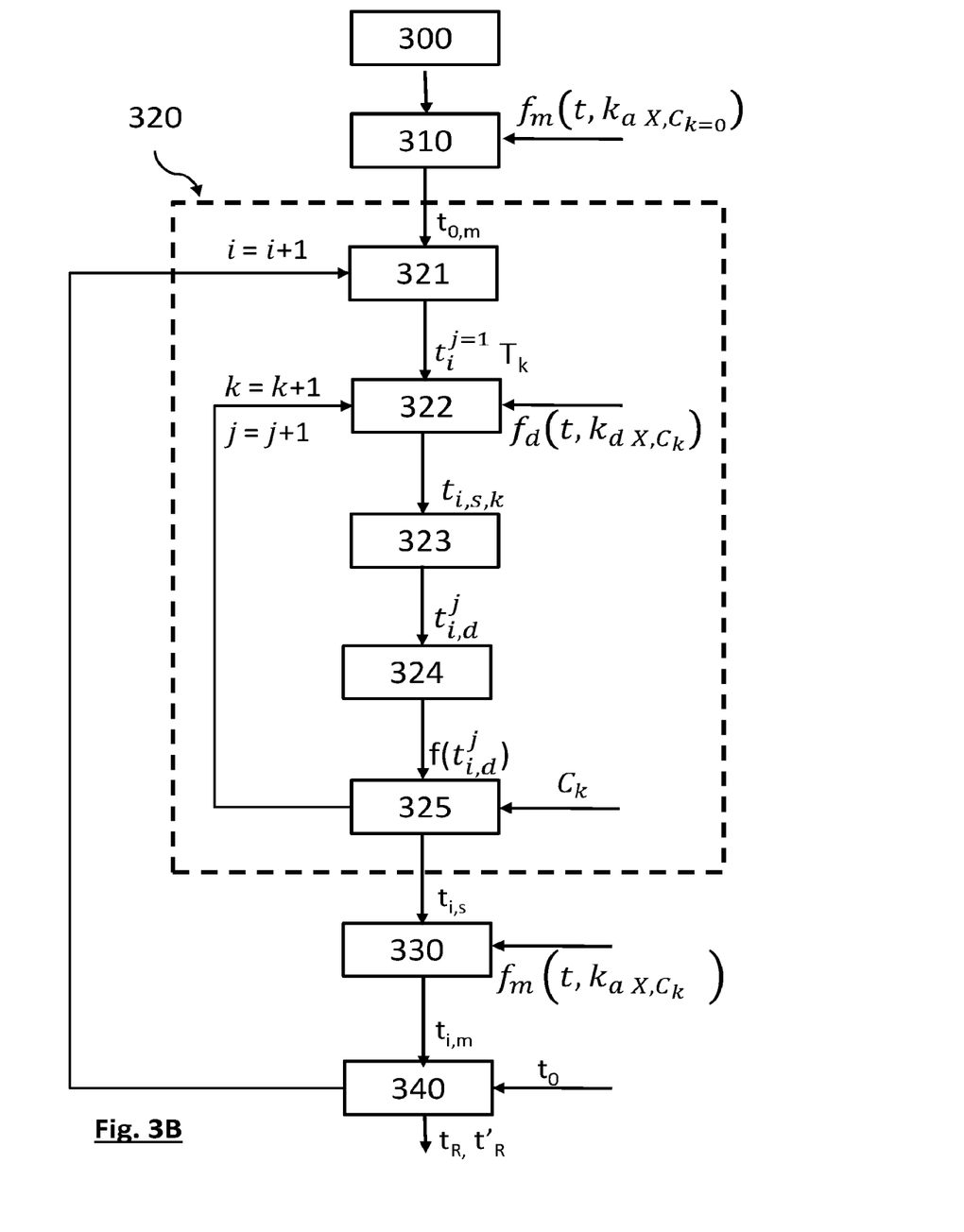

FIG. 2 shows a first embodiment of a method according to the invention, in which the operating parameters of the column are constant during the transit of a particle. The particle x is, in this example, a gas molecule.

Step 100: initialization. The molecule x is introduced into the column.

Step 110: determination of the transit time before the first adsorption. This step comprises carrying out random sampling conditioned by the first probability law to establish a time $t_{0,m}$ passed in the mobile phase before a first adsorption.

The method then follows an iterative process, the index i designating the rank of the iteration.

Step 120: on each adsorption i, sampling conditioned by the second probability law is carried out to establish a time $t_{i,S}$ passed by the molecule in the stationary phase during said adsorption.

Step 130: on each desorption following an adsorption i, random sampling conditioned by the first probability law is carried out to establish a time $t_{i,m}$ passed in the mobile phase following the $i^{th}$ adsorption.

Step 140: reiteration or exit from the algorithm. In step 140, the index i is incremented and steps 120 and 130 are reiterated until the cumulative time passed in the mobile phase reaches the dead time $t_0$. This reiteration condition corresponds to $$\Sigma_{l=0}^{i} t_{i,m} \geq t_0 \qquad (3).$$

When this condition is satisfied, step 140 determines the time passed by the particle x in the column, which time is called the retention time and denoted $t_R$, using the expression $$\Sigma_{l=0}^{Ni} t_{l,s} + t_0 = t_R \qquad (4)$$

where $N_i$ represents the number of iterations carried out, i.e. the number of adsorptions in the stationary phase.

It is also possible to define what is called an adjusted retention time $t'_R$ corresponding to the cumulative time passed by the particle x in the stationary phase, i.e. $\Sigma_{l=0}^{Ni} t_{l,s} = t'_R$ (4').

A second embodiment will now be described with reference to FIG. 3A, in which embodiment the temperature of the column is modulated. More precisely, during the transit of the molecule x through the column, the temperature T varies according to a predetermined function of time. To each time t corresponds a column temperature T such that $T = f(t)$, $f$ being a function describing the temporal variation of the temperature.

For example, the column is brought in succession to $N_k$ temperature plateaus $T_k$, k being a strictly positive integer representing the rank of each temperature plateau. A temperature modulation corresponds to a succession of temperature plateaus in a predetermined order. The temperature variation function $f$ may then be expressed by the expression:

$$f(t) = T_k = T_i + \frac{T_f - T_i}{N_K} \sum_{k=1}^{N_k} H\left(t - \left\|k \times \frac{t_f}{N_K}\right\|\right) \qquad (5)$$

where:
  $T_i$ is an initial temperature of the temperature modulation, this temperature for example corresponding to the entrance of the particle into the column;
  $t_f$ is the duration of the temperature modulation of the column;
  $T_f$ is the final temperature of the column, during the last plateau; and
  H is the Heaviside function, where $H(t)=0$ if $t<0$ and $H(t)=1$ if $t \geq 0$.

In this embodiment it is assumed that the dead time $t_0$ is independent of the temperature variation. Thus, according to this first approach, the first probability law is considered not to depend on temperature, the adsorption coefficient $k_a$ being considered to be independent of temperature. The second probability law depends on temperature, because of the variation in the ratio $$\frac{k_a}{k_d}$$

as a function of temperature, which is expressed by the Van't Hoff equation:

$$\frac{k_a}{k_d} = \frac{1}{\beta} e^{-\frac{\Delta H}{RT} + \frac{\Delta S}{R}} \qquad (6)$$

where:
  $\Delta H$ is the enthalpy of activation, the value of which depends on the material composing the stationary phase and on temperature;
  $\Delta S$ is the entropy of activation the value of which depends on the material composing the stationary phase and on temperature;
  R is the ideal gas constant;
  $\beta$ is the ratio of the phases, i.e. the volume of the mobile phase over the volume of the stationary phase.

It becomes:

$$k_d = \beta k_a e^{\frac{\Delta H}{RT} + \frac{\Delta S}{R}}. \qquad (6')$$

The following are the various steps of this embodiment:

Step 200: initialization: the temperature $T_k$ is initialized to $T_{k=1}$.

Step 210: determination of the transit time in the mobile phase before a first adsorption. This step comprises carrying out random sampling conditioned by the first probability law to establish a time $t_{0,m}$ passed in the mobile phase before a first adsorption.

The method then follows an iterative process, the index i designating the rank of the iteration.

Step 220: on each adsorption i, a time $t_{i,S}$ passed by the particle in the stationary phase during said adsorption is determined. This step takes into account the fact that during an adsorption i the temperature of the stationary phase is liable to change. It encompasses various substeps that are carried out iteratively, the index j designating the rank of these iterations, this index being initialized at 1. A temperature plateau $T_k$ is associated with each index j. The index j=1 corresponds to the temperature plateau $T_k$ during which the adsorption i takes place, the following indices corresponding to the following temperature plateaus $T_{k+i}$, $T_{k+2}$, etc.

Substep 221: determination of the time denoted $t_i^{j=1}$ at which the adsorption of rank i takes place, and determination of the temperature $T_k$ corresponding to this time by application of the temperature variation function $T_k = f(t_i^{j=1})$.

The time $t_i^{j=1}$ at which adsorption i takes place is obtained by $t_i^{j=1} \Sigma_{l=0}^{i-1} t_{l,m} + \Sigma_{l=1}^{i-1} t_{l,s}$ (7) where:
  $\Sigma_{l=0}^{i-1} t_{l,m}$ + is the sum of the times $t_{l,m}$ passed in the mobile phase until the adsorption i; on the first adsorption (i=1) this term is equal to $t_{0,m}$;
  $\Sigma_{l=1}^{i-1} t_{l,s}$ is the sum of the times $t_{l,s}$ passed in the stationary phase until the adsorption i; on the first adsorption (i=1) this term is zero.

Substep 222: estimating a time spent adsorbed in the stationary phase during the adsorption i and during the temperature plateau $T_k$ associated with the iteration index j by carrying out random sampling conditioned by the second probability law to establish a time $t_{i,s,k}$ passed in the stationary phase, during the adsorption i and during the temperature plateau $T_k$. This estimation is determined by carrying out random sampling according to the second probability law:

when j=1, at the time $t_i^{j=1}$ at which the $i^{th}$ adsorption takes place, said time being determined in substep 221;

when j>1, at the time $t_i^j$ corresponding to the start of the temperature plateau $T_k$ associated with the iteration j.

Substep 223: on the basis of the sampling of $t_{i,s,k}$ estimating a desorption time $t_{i,d}^j$ associated with the iteration j using the expression:

$$t_{i,d}^j = t_i^j + t_{i,s,k} \quad (8).$$

This estimation is valid only if, at the desorption time $t_{i,d}^j$, the temperature of the column corresponds to the temperature $T_k$ used to estimate the time $t_{i,s,k}$ passed in the stationary phase. In other words, this estimation is valid if the temperature does not change between the times $t_{i,d}^j$ and $t_{i,d}^j$. This is the subject matter of steps 224 and 226.

Substep 224: estimating the temperature of the column, at the desorption time $t_{i,d}^j$ determined in step 223, by applying the temperature variation function $f(t_{i,d}^j)$.

Substep 225: validating the estimation of the desorption time $t_{i,d}^j$ estimated in step 223 by comparing the temperature $f(t_{i,d}^j)$ at the estimated desorption time $t_{i,d}^j$ and the temperature $f(t_i^j)$ at which this time was estimated:

If $f(t_{i,d}^j) \neq f(t_i^j)$, i.e. if the temperature at the desorption time $t_{i,d}^j = t_i^j + t_{i,s,k}$ is different from the temperature $T_k$ at which the adsorption time $t_{i,s,k}$ was estimated, the estimation of the desorption time $t_{i,d}^j$ associated with the iteration j is invalid. Specifically, this means that the temperature of the column changed between the time $t_i^j$ at which the adsorption time $t_{i,s,k}$ was estimated and the desorption time $t_{i,d}^j$.

In this case, a new iteration j+1 is carried out starting from substep 222, the adsorption time $t_i^{j+1}$ being considered to correspond to the start of the temperature plateau $T_{k+1}$ following the temperature plateau $T_k$ corresponding to the iteration j.

In other words, $t_i^{j+1} = \sum_{q=1}^{q=k} \Delta t_q$ (9) where $\Delta t_q$ represents the length of the temperature plateau of rank q, and k represents the rank of the temperature step corresponding to the current iteration: $T_k f(t_i^j)$. Substeps 221 to 225 are then reiterated with a column temperature $T = T_{k+1} = f(t_i^{j+1})$. Thus, because of the temporal shift achieved by updating the adsorption time according to expression (9), in each new iteration j the particle is considered to be adsorbed in a stationary phase brought to a temperature $T_k = f(t_i^j)$ and in which phase the adsorption time is conditioned by the probability law $f_d(t, k_{d\,X,P=T}) = k_{d\,X,T} \times e^{-t \times k_{d\,X,T}}$. The chromatography column is then considered to be a succession of $N_k$ independent elementary columns, each elementary column being raised to a temperature $T_k$.

If $f(t_{i,d}^j) = f(t_i^j)$, i.e. if the temperature at the estimated desorption time $t_{i,d}^j$ corresponds to the temperature at which the adsorption time $t_{i,s,k}$ was estimated, the estimation of the desorption time is valid. The step 230 is then passed to, the time passed in the stationary phase S during the adsorption i being considered to be such that $t_{i,s} = t_{i,d}^j + t_{i,s,k} t_{i,d}^{j-1}$ (10).

Step 230: on each desorption following an adsorption i, carrying out random sampling conditioned by the first probability law to estimate a time $t_{i,m}$ passed in the mobile phase between the adsorption of rank i and the adsorption of rank i+1.

Step 240: following iteration or exit from the algorithm. Steps 220 and 230 are reiterated and the index i incremented until the cumulative time passed in the mobile phase reaches the dead time $t_0$, just like in the preceding embodiment. This condition corresponds to:

$$\sum_{l=0}^{i} t_{l,m} \geq t_0$$

When this condition is met, step 240 determines the time passed by the particle in the column, called the retention time and denoted $t_R$, such that $$\sum_{l=0}^{i} t_{l,s} + t_0 = t_R$$

It is also possible to define what is called an adjusted retention time $t'_R$ corresponding to the time passed by the particle in the stationary phase, namely: $\sum_{l=1}^{i} t_{l,s} = t'_R$.

This method is implemented for a plurality of particles x of a given species X so as to determine a distribution of the retention time $t_R$ or of the adjusted retention time $t'_R$ for said species X. It is then possible to estimate statistical parameters relating to this distribution, such as a mean, a parameter representative of a dispersion, for example the variance or standard deviation, or other parameters. The method then allows a chromatogram corresponding to said species X to be estimated without recourse to an analytical expression.

Use of a stochastic method makes it possible to carry out, on each adsorption, sampling according to a probability law taking into account the variation in the temperature of the column. It will be understood that such sampling is carried out sequentially, thereby allowing the temperature conditions at the time of which the sampling is carried out to be taken into account. The method is therefore particularly adapted to the case where the temperature of the stationary phase varies during the transit of the particle through the column.

More generally, the method is adapted to any temporal or spatial variation of a parameter of the column during the transit of a particle. This variation leads to a modellable variation in the first probability and/or the second probability laws that were described above, during this transit. It is then possible to model a retention time via an estimation of the time passed by the particle in the stationary phase during each adsorption. It will furthermore be understood that apart from a temporal variation in the temperature of the column, the method is suitable for modelling a temporal variation in the composition C of the mobile phase M (i.e. the carrier fluid), or even a spatial variation in the composition of the stationary phase S.

According to a third embodiment, the composition C of the mobile phase M varies as a function of time between various plateaus. In this case, a temporal variation function g describes the variation of this composition as a function of time. Thus, in this embodiment, the composition of the mobile phase varies between plateaus $C_k$ such that $C_k = g(t)$. The main steps of this embodiment are described below, with regard to FIG. 3B.

Step 300 is an initialization step in which the composition of the mobile phase is initialized such that $C = C_{k=0}$. Step 310 corresponds to the step 210 described above. At the end of this step, the method follows an iterative process analogous to that described with regard to FIG. 3A, the index i designating the rank of the iteration. In this embodiment, the first probability law may vary as a function of the composition of the mobile phase.

Step 320: on each adsorption i, determining the time $t_{i,s}$ passed by the particle in the stationary phase. This step takes into account the fact that during an adsorption i the composition of the mobile phase is liable to change. It encompasses various substeps, which are carried out iteratively, in a similar way to the preceding embodiment. The index j designates the rank of the iteration, this index being initialized to 1. With each index j is associated a composition of the mobile phase $C_k$. The index $j=1$ corresponds to the composition of the mobile phase on the adsorption i, the following indices corresponding to the plateaus of following compositions $C_{k+1}$, $C_{k+2}$, etc.

Substep 321: determining the time, denoted $t_i^{j=1}$, at which the adsorption of rank i takes place and determining the composition of the mobile phase at this time by applying the mobile-phase variation function $C_k = g(t_i^{j=1})$. This adsorption time is obtained in the same way in the substep 221 described above.

Substep 322: estimating a time spent adsorbed in the stationary phase, during the adsorption i, when the mobile phase has the composition $C_k$, by carrying out random sampling conditioned by the second probability law to establish a time $t_{i,s,k}$ passed in the stationary phase, during the adsorption while the mobile phase has the composition $C_k$.

This estimation is determined by carrying out random sampling according to the second probability law:
 when $j=1$, at the time $t_i^{j=1}$ at which the $i^{th}$ adsorption takes place, said time being obtained in substep 321;
 when $j>1$, at the time $t_i^j$ corresponding to the start of the temperature plateau $C_k$ associated with the iteration j.

Substep 323: On the basis of the sampling of $t_{i,s,k}$, estimating a desorption time $t_{i,d}^j$ associated with the iteration j using the expression:

$$t_{i,d}^j = t_i^j + t_{i,s,k} \quad (8).$$

This estimation is valid only if, at the desorption time $t_{i,d}^j$, the composition of the mobile phase corresponds to the composition $C_k$ used to estimate the time $t_{i,s,k}$ passed in the stationary phase. In other words, this estimation is valid if the composition of the mobile phase does not change between the times $t_{i,d}^j$ and $t_i^j$. This is the subject matter of substeps 324 and 326.

Substep 324: estimating the composition of the mobile phase of the column, at the desorption time $t_{i,d}^j$ determined in substep 323, by applying the function $g(t_{i,d}^j)$ describing the variation in the composition of the mobile phase.

Substep 325: validating the estimation of the desorption time $t_{i,d}^j$ estimated in step 324 by comparing the composition of the mobile phase $g(t_{i,d}^j)$ at the estimated desorption time $t_{i,d}^j$ and the composition of the mobile phase $g(t_i^j)$ at which this time was estimated:
 If $g(t_{i,d}^j) \neq g(t_i^j)$, i.e. if the composition of the mobile phase at the estimated desorption time is different from the composition $C_k$ at which the adsorption time $t_{i,s,k}$ was estimated, the estimation of the desorption time $t_{i,d}^j$ associated with the iteration j is invalid. Specifically, this means that the composition of the mobile phase changed between the adsorption time $t_i^j$ at which the adsorption time $t_{i,s,k}$ was estimated and the desorption time $t_{i,d}^j$.

In this case, a new iteration j+1 is carried out starting from substep 322, the adsorption time $t_i^{j+1}$ being considered to correspond to the start of the composition plateau $C_{k+1}$ following the composition plateau $C_k$ corresponding to the iteration j.

In other words, $t_i^{j+1} = \Sigma_{q=1}^{q=k} = \Delta t_q$ where $\Delta t_q$ represents the length of the composition step of rank q, and k represents the rank of the composition step corresponding to the current iteration: $C_k = g(t_i^j)$.

Substeps 321 to 325 are then reiterated with a composition of the mobile phase such that $C_{k+1} = g(t_i^{j+1})$.

If $g(t_{i,d}^j) = g(t_i^j)$, i.e. if the composition of the mobile phase at the estimated desorption time $t_{i,d}^j$ corresponds to the composition of the mobile phase with which the adsorption time $t_{i,s,k}$ was estimated, the estimation of the desorption time is valid. The step 330 is then passed to, the time passed in the stationary phase S during the adsorption i being considered to be such that $t_{i,s} = t_{i,d}^j + t_{i,s,k} - t_{i,d}^{j-1}$.

Step 330: on each desorption following an adsorption i, carrying out sampling conditioned by the first probability law to determine a time $t_{i,m}$ passed in the mobile phase between the adsorption of rank i and the adsorption of rank i+1. The first probability law may depend on the composition of the mobile phase, because of the dependence of the adsorption rate $k_a$.

Step 340: following iteration or exit from the algorithm. Steps 320 to 330 are reiterated and the index i incremented until the cumulative time passed in the mobile phase reaches the dead time $t_0$, just like in the preceding embodiment and analogously to step 240. When this condition is met, step 340 determines the time passed by the particle in the column, or the adjusted retention time, depending on the cumulative time passed in the stationary phase.

In a fourth embodiment, the composition $C_S$ of the stationary phase S varies spatially as a function of a distance with respect to the entrance of the column. Thus, it is possible to determine a stationary-phase variation function h such that $C_S = h(D_i)$, $D_i$ representing a distance at which an adsorption i occurs with respect to the entrance of the column. On each adsorption, a second probability law corresponding to the composition Cs of the stationary phase corresponding to the distance $D_i$ is used.

Trials

Figure 4A:
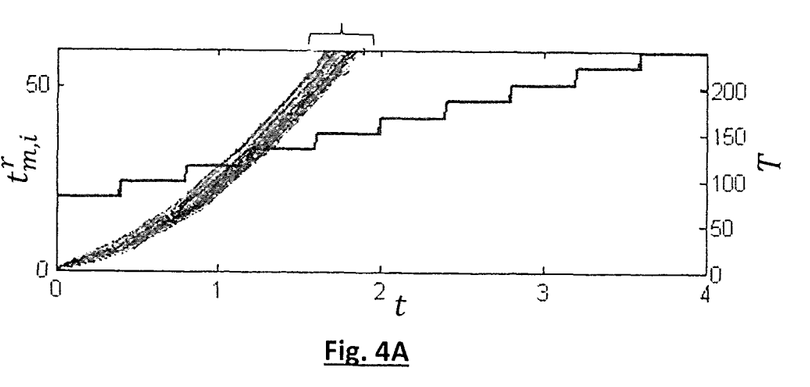
FIG. 4A shows the result of simulations of the transit of 500 particles of a given species. It shows the variation as a function of cumulative time passed, by each molecule, in the mobile phase, between each adsorption.

Simulations were carried out simulating the transit of 500 molecules of anthracene, the temperature of the column being modulated in ten temperature plateaus of the same length, between an initial temperature $T_i = 60°$ C. at t=0 min and a final temperature $T_f = 240°$ C. at t=4 mins. The molecules were introduced into the column at t=0 min. FIG. 4A shows on the same graph:
 the temperature variation function $T_k = f(t)$, k here being comprised between 1 and 10.
 the cumulative time passed, for each run r, in the mobile phase, until an adsorption i, the index i varying as a function of the time t. This cumulative time passed in the mobile phase is denoted $t_{m,i}^r$ and is determined by the expression $t_{m,i}^r = \Sigma_{l=0}^i t_{m,l}^r + (11)$, $t_{m,l}^r$ designating the time in the mobile phase following an adsorption l, $t_{m,l=0}^r$ designating the time passed in the mobile phase before the first adsorption. The curly bracket placed on the graph shows the range over which the retention times $t_R^r$ of each run extended, said times corresponding to the experimental time t when the cumulative desorbed time equaled the dead time which, for this column, was 60 s.

In this trial, a column of 30 meters length and 0.25 mm diameter was considered, the stationary phase of which was 0.25 μm thick and of the following composition: 5% phenyl arylene, 95% dimethylpolysiloxane.

Figure 4B:
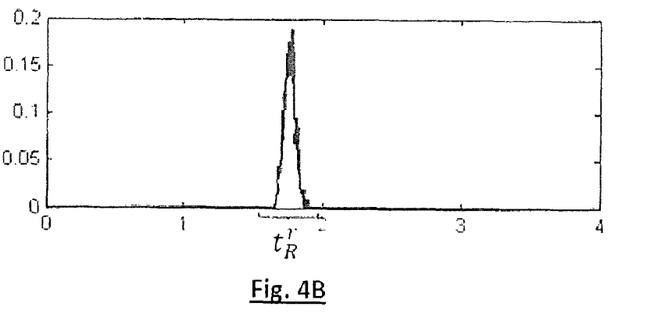
FIG. 4B shows the distribution of the retention time in the column for the set of modelled transits.

FIG. 4B shows the distribution of the retention time in this column, which distribution was established using 500 runs. It is a question of the histogram of the retention times $t_R^r$ for each run r, where $1 \leq r \leq 500$. This distribution constitutes a direct model of the column for this temperature variation and for the molecule anthracene. The greater the number of runs, the higher the statistical precision of the direct model.

Moreover, simulations were carried out using five compounds of polycyclic aromatic hydrocarbon (PAH) type: acenaphthene (ACE), fluoranthene (FTN), benzo(a)pyrene (B(a)P), anthracene (ANT) and indeno(1,2,3-cd)pyrene (IND). For each of these molecules, a column of 30 m length and 250 μm diameter was considered, the stationary phase consisting of a mixture of 5% phenyl arylene and 95% dimethylpolysiloxane and having a thickness of 0.25 μm. For each species, a distribution of adjusted retention times was established, from which an average adjusted retention time was estimated. These average retention times are shown, in FIG. 5, for each molecule, in the form of vertical lines.

Experimental trials were carried out using a methanol solution containing the five aforementioned compounds, the concentration of each of them being 100 μg/mL. The chromatography column was coupled to a flame ionization detector.

Figure 5:
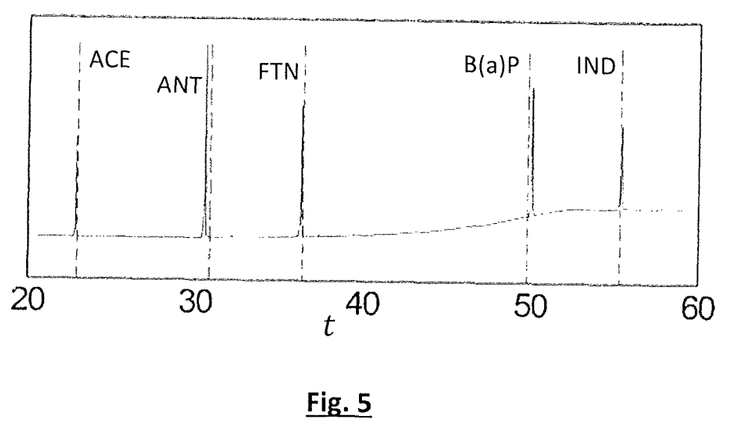
FIG. 5 shows estimations of the mean adjusted retention time of various molecules, which estimations were obtained according to a method according to the invention, overlaid on an experimental chromatogram of a mixture comprising said molecules.

In the simulations, as in the experimental trials, the column was subjected to a temperature gradient of 5° C. per minute, between an initial temperature of 50° C. and a final temperature of 250° C. The duration of each plateau was about 5 s. The chromatogram, corrected for the dead time of the column, is shown in FIG. 5. The good correlation of the adjusted retention time of each species, between the experimental trials and the results of the modelling, will be noted.

The method described above applies both to the modelling of liquid-phase and gas-phase chromatography columns. It may also be applied to multidimensional chromatography, which consists in placing various columns in series. This method may be implemented while a chromatography column is being dimensioned or while the operating parameters of a column are being optimized. It may also be used to establish a direct model of the column for use when processing measurements.

The invention claimed is:

1. A method for obtaining and processing a chromatogram, the chromatogram being processed based on a plurality of estimations of a retention time of particles of a species in a chromatography column, said chromatography column including a channel, one wall of which is formed from a coating, called the stationary phase, able to adsorb and desorb each particle, the latter being carried by a carrier fluid, called the mobile phase, transiting said column between an entrance and an exit, defining a dead time, the method comprising:
   a) estimating, using a processor, a time passed in the mobile phase after the entrance of a particle of the species into the column and until a first adsorption in the stationary phase using a probability law of the time passed by the particle in said mobile phase, which probability law is called the first probability law;
   b) following each adsorption of the particle in the stationary phase, estimating, using the processor, a time passed by the particle in the stationary phase until a desorption using a probability law of the time passed by the particle in the stationary phase, which probability law is called the second probability law;
   c) following each desorption from the stationary phase, estimating, using the processor, a time passed by the particle in the mobile phase until a new adsorption in the stationary phase, using said first probability law; and
   d) repeating said steps b) and c), using the processor, until a sum of the estimations of the time passed in the mobile phase is greater than the dead time; and
   e) summing, using the processor, the estimations of the times passed by the particle in the stationary phase, in order to estimate the retention time of the particle in the column,
wherein the method further comprises:
detecting, using a detector, a plurality of particles of the species exiting the column as a function of time to obtain the chromatogram; and
analyzing the obtained chromatogram, including processing based on the plurality of estimations of the retention time of particles of the species,
wherein during the transit of the particle between the entrance and the exit, at least one parameter governing operation of the column is controlled so as to vary, the first probability law and/or the probability law varying as a function of said at least one parameter,
wherein said step b) includes:
   estimating a desorption time of the particle using a value of the the at least one parameter,
   estimating a value of the at least one parameter at the estimated desorption time, and
   comparing the estimated value of the at least one parameter at the estimated desorption time with the value of the parameter used for estimating the desorption time,
wherein the at least parameter is at least one of:
   a temperature of the column, and
   a composition of the mobile phase, said at least one parameter being varied as a function of time between a plurality of plateaus,
wherein during the transit of the particle, the at least one parameter of the column is successively brought to various plateaus of the plurality of plateaus, said various plateaus corresponding to respective values of the at least one parameter and being attributed respective ranks, and
wherein said step b) includes the following substeps:
   i) estimating the absorption time at which said adsorption takes place and determining the at least one parameter of the column at said absorption time,
   ii) estimating a time passed by the particle in the stationary phase until a desorption using a probability law dependent on time passed in the stationary phase, this probability law also depending on a value of the at least one parameter at said adsorption time,
   iii) estimating a desorption time of the particle from the estimation established in said substep ii),
   iv) determining a value of the at least one parameter corresponding to said desorption time, and
   v) when said value of the at least one parameter at said desorption time is different from the value used in said substep ii), reiterating said substeps ii) to iv) using the adsorption time corresponding to the start of the plateau of following rank, and when the value of the at least one parameter at said desorption time corresponds to the value used in said substep ii), determining a time passed in the stationary phase during said adsorption.

2. The method of claim 1, wherein the at least one parameter includes a composition of the stationary phase, said composition being controlled so as to vary between the entrance and the exit of the column.

3. The method of claim 1, wherein, in said substep v), said time passed in the stationary phase is obtained depending on:
- a length of each plateau between the adsorption time determined in said substep i) and before the last iteration of said substeps ii) to v), and
- the estimation of the time passed in the stationary phase, which time is estimated in said last iteration of said substeps ii) to v).

4. The method of claim 1, wherein, in said step a) or said step c), said first probability law follows an exponential distribution parameterized by an adsorption rate, the latter representing a probability per unit time that said particle in the mobile phase will be adsorbed in the stationary phase.

5. The method of claim 1, wherein, in said step b), said second probability law dependent on time passed in the stationary phase follows an exponential distribution parameterized by a desorption rate, the latter representing a probability per unit time that said particle in the stationary phase will be desorbed by said stationary phase.

6. The method of claim 1, wherein said dead time corresponds to an average time passed by a particle, of a species or type different from the species or a type of the plurality of particles, transported by the carrier fluid, in said column without adsorption in the stationary phase.

7. The method of claim 1, wherein said steps a) to e) are carried out for a plurality of particles of various species, including said plurality of particles, so as to obtain a retention time distribution for each of the various species.

8. The method of claim 7, further comprising a step f) of determining a statistical indicator, which is an average of at least one distribution of retention time of the species associated with the plurality of particles.

9. A processor-readable non-transitory data storage medium including instructions for executing a method according to claim 1, these instructions being able to be executed by the processor.

* * * * *